(12) United States Patent
Putzig

(10) Patent No.: US 8,236,739 B2
(45) Date of Patent: *Aug. 7, 2012

(54) ZIRCONIUM-BASED CROSS-LINKER COMPOSITIONS AND THEIR USE IN HIGH PH OIL FIELD APPLICATIONS

(75) Inventor: Donald Edward Putzig, Newark, DE (US)

(73) Assignee: Dork Ketal Speciality Catalysts, LLC, Stafford, TX (US)

( * ) Notice: Subject to any disclaimer, the term of this patent is extended or adjusted under 35 U.S.C. 154(b) by 164 days.

This patent is subject to a terminal disclaimer.

(21) Appl. No.: 11/731,049

(22) Filed: Mar. 30, 2007

(65) Prior Publication Data

US 2008/0242563 A1    Oct. 2, 2008

(51) Int. Cl.
*C09K 8/04* (2006.01)
*C09K 3/00* (2006.01)

(52) U.S. Cl. .................. 507/271; 507/211; 252/182.13

(58) Field of Classification Search .................. 507/271
See application file for complete search history.

(56) References Cited

U.S. PATENT DOCUMENTS

| | | |
|---|---|---|
| 2,824,114 A | 2/1958 | Bostwick |
| 2,824,115 A | 2/1958 | Beacham et al. |
| 2,894,966 A | 7/1959 | Russell |
| 3,525,690 A | 8/1970 | Christian |
| 3,888,312 A | 6/1975 | Tiner et al. |
| 2,978,347 A | 4/1981 | Koehler et al. |
| 4,382,874 A | 5/1983 | Jenkins |
| 4,460,751 A | 7/1984 | Hanlon et al. |
| 4,477,360 A | 10/1984 | Almond |
| 4,488,975 A | 12/1984 | Almond |
| 4,524,829 A | 6/1985 | Hanlon et al. |
| 4,534,870 A | 8/1985 | Williams |
| 4,553,601 A | 11/1985 | Almond et al. |
| 4,578,488 A | 3/1986 | Rummo et al. |
| 4,579,670 A | 4/1986 | Payne |
| 4,657,081 A | 4/1987 | Hodge |
| 4,677,201 A | 6/1987 | Morgan |
| 4,683,068 A | 7/1987 | Kucera |
| 4,686,052 A | 8/1987 | Baranet et al. |
| 4,702,848 A | 10/1987 | Payne |
| 4,749,041 A | 6/1988 | Hodge |
| 4,797,216 A | 1/1989 | Hodge |
| 4,798,902 A | 1/1989 | Putzig |
| 4,883,605 A | 11/1989 | Putzig |
| 5,165,479 A | 11/1992 | Harris et al. |
| 5,217,632 A | 6/1993 | Sharif |
| 5,271,466 A | 12/1993 | Harms |
| 5,273,580 A | 12/1993 | Totten et al. |
| 5,305,832 A | 4/1994 | Gupta et al. |
| 5,462,683 A | 10/1995 | Kinoshita et al. |
| 5,466,846 A | 11/1995 | Sharif |
| 5,478,802 A * | 12/1995 | Moradi-Araghi ............. 507/203 |
| 5,512,188 A | 4/1996 | Kinoshita et al. |
| 5,547,025 A | 8/1996 | Ahmed et al. |
| 5,558,161 A | 9/1996 | Vitthal et al. |
| 5,569,643 A | 10/1996 | Kinoshita et al. |
| 5,614,475 A * | 3/1997 | Moorhouse et al. ........... 507/273 |
| 5,642,783 A | 7/1997 | Moradi-Araghi et al. |
| 5,650,633 A | 7/1997 | Ahmed et al. |
| 5,688,894 A | 11/1997 | Ridland |
| 5,708,107 A | 1/1998 | Ahmed et al. |
| 5,785,747 A | 7/1998 | Vollmer et al. |
| 5,789,350 A | 8/1998 | Moradi-Araghi et al. |
| 5,789,351 A | 8/1998 | Ahmed et al. |
| 5,798,320 A | 8/1998 | Dawson et al. |
| 5,849,674 A | 12/1998 | Fox et al. |
| 5,883,210 A | 3/1999 | Ahmed et al. |
| 5,922,653 A | 7/1999 | Ahmed et al. |
| 5,950,731 A | 9/1999 | Shuchart et al. |
| 6,051,670 A | 4/2000 | Ahmed et al. |
| 6,186,235 B1 | 2/2001 | Tjon-Joe-Pin et al. |
| 6,214,773 B1 | 4/2001 | Harris et al. |
| 6,333,423 B1 | 12/2001 | Kol et al. |
| 6,387,986 B1 | 5/2002 | Moradi-Araghi et al. |
| 6,454,008 B1 | 9/2002 | Chatterji et al. |
| 6,488,091 B1 | 12/2002 | Weaver et al. |
| 6,613,720 B1 | 9/2003 | Feraud et al. |
| 6,734,146 B2 | 5/2004 | Chatterji et al. |
| 6,737,386 B1 | 5/2004 | Moorhouse et al. |
| 6,793,018 B2 | 9/2004 | Dawson et al. |
| 6,810,959 B1 | 11/2004 | Qu et al. |
| 6,814,145 B2 | 11/2004 | Maberry et al. |

(Continued)

FOREIGN PATENT DOCUMENTS

EP         0138522 A2 *   4/1985

(Continued)

OTHER PUBLICATIONS

U.S. Appl. No. 11/643,513, filed Dec. 21, 2006, Putzig.
Office Action (Final) dated Mar. 21, 2011 (20 pages), U.S. Appl. No. 11/643,513, filed on Dec. 21, 2006.
Advisory Action dated May 31, 2011 (3 pages), U.S. Appl. No. 11/643,513, filed on Dec. 21, 2006.
BASF Technical Bulletin entitled "Quadrol® polyol," 2002, 1 page, BASF Corporation.
Office Action dated Jul. 14, 2009 (17 pages), U.S. Appl. No. 12/074,953, filed on Mar. 7, 2008.
Office Action (Final) dated Mar. 11, 2010 (13 pages), U.S. Appl. No. 12/074,953, filed on Mar. 7, 2008.
Office Action dated Sep. 12, 2011 (14 pages), U.S. Appl. No. 11/643,513, filed on Dec. 21, 2006.

(Continued)

*Primary Examiner* — Peter F Godenschwager
(74) *Attorney, Agent, or Firm* — Conley Rose, P.C.; Rodney B. Carroll

(57) ABSTRACT

A cross-linking composition which comprises (a) an aqueous liquid, (b) a cross-linkable organic polymer, and (c) a solution comprising a zirconium cross-linking agent which comprises a zirconium complex having a molar ratio of 1:2 to 1:4 of zirconium to triethanolamine and a molar ratio of 1:0.1 to 1:1 of zirconium to N,N,N',N'-tetrakis-(2-hydroxypropyl)-ethylene diamine. The composition can be used in oil field applications for hydraulic fracturing and plugging of permeable zones and leaks in subterranean formations.

28 Claims, No Drawings

U.S. PATENT DOCUMENTS

| | | |
|---|---|---|
| 6,818,598 B2 | 11/2004 | Maberry et al. |
| 6,918,445 B2 | 7/2005 | Todd et al. |
| 6,971,448 B2 | 12/2005 | Slabaugh et al. |
| 6,983,801 B2 | 1/2006 | Dawson et al. |
| 6,986,391 B2 | 1/2006 | Funkhouser et al. |
| 7,001,872 B2 | 2/2006 | Pyecroft et al. |
| 7,036,590 B2 | 5/2006 | Harris |
| 7,078,370 B2 | 7/2006 | Crews |
| 7,140,438 B2 | 11/2006 | Frost et al. |
| 7,151,076 B2 | 12/2006 | Qu et al. |
| 7,165,617 B2 | 1/2007 | Lord et al. |
| 7,297,665 B2 | 11/2007 | Harris et al. |
| 7,347,265 B2 | 3/2008 | Monroe et al. |
| 7,730,952 B2 | 6/2010 | Putzig |
| 7,732,383 B2 | 6/2010 | Putzig |
| 7,795,187 B2 | 9/2010 | Putzig |
| 7,795,188 B2 | 9/2010 | Putzig |
| 2003/0092584 A1 | 5/2003 | Crews |
| 2003/0114539 A1 | 6/2003 | Weaver et al. |
| 2003/0119678 A1 | 6/2003 | Crews |
| 2004/0211568 A1 | 10/2004 | Funkhouser et al. |
| 2004/0214724 A1 | 10/2004 | Todd et al. |
| 2004/0238169 A1 | 12/2004 | Todd et al. |
| 2005/0034868 A1 | 2/2005 | Frost et al. |
| 2005/0077044 A1 | 4/2005 | Qu et al. |
| 2005/0137094 A1 | 6/2005 | Weaver et al. |
| 2005/0215425 A1 | 9/2005 | Clair et al. |
| 2005/0269099 A1 | 12/2005 | Stegent et al. |
| 2005/0284637 A1 | 12/2005 | Stegent et al. |
| 2006/0009363 A1 | 1/2006 | Crews |
| 2006/0027364 A1 | 2/2006 | Kelly et al. |
| 2006/0030493 A1 | 2/2006 | Segura |
| 2006/0247135 A1 | 11/2006 | Welton et al. |
| 2006/0264334 A1 | 11/2006 | Gupta et al. |
| 2006/0283597 A1 | 12/2006 | Schriener et al. |
| 2007/0187098 A1 | 8/2007 | Putzig |
| 2007/0187102 A1 | 8/2007 | Putzig |
| 2009/0227479 A1 | 9/2009 | Putzig |

FOREIGN PATENT DOCUMENTS

| | | | |
|---|---|---|---|
| EP | 0278684 | A1 | 8/1988 |
| EP | 0449384 | A1 | 10/1991 |
| EP | 0558099 | B1 | 9/1993 |
| GB | 2108122 | A * | 5/1983 |
| JP | 2000264893 | A | 9/2000 |
| WO | 2006010912 | A1 | 2/2006 |
| WO | 2007095018 | A2 | 8/2007 |
| WO | 2007095018 | A3 | 8/2007 |
| WO | 2007095367 | A2 | 8/2007 |
| WO | 2008082504 | A1 | 7/2008 |
| WO | 2008121357 | A1 | 10/2008 |

OTHER PUBLICATIONS

Notice of Allowance dated Dec. 2, 2011 (26 pages), U.S. Appl. No. 12/074,953, filed on Mar. 7, 2008.

Office Action (Final) dated Dec. 19, 2011 (11 pages), U.S. Appl. No. 11/643,513, filed on Dec. 21, 2006.

* cited by examiner

ZIRCONIUM-BASED CROSS-LINKER COMPOSITIONS AND THEIR USE IN HIGH PH OIL FIELD APPLICATIONS

FIELD OF THE INVENTION

The present invention relates to zirconium chelates and their use in oil field applications such as hydraulic fracturing and plugging of permeable zones.

BACKGROUND OF THE INVENTION

The production of oil and natural gas from an underground well (subterranean formation) can be stimulated by a technique called hydraulic fracturing, in which a viscous fluid composition (fracturing fluid) containing a suspended proppant (e.g., sand, bauxite) is introduced into an oil or gas well via a conduit, such as tubing or casing, at a flow rate and a pressure which create, reopen and/or extend a fracture into the oil- or gas-containing formation. The proppant is carried into the fracture by the fluid composition and prevents closure of the formation after pressure is released. Leak-off of the fluid composition into the formation is limited by the fluid viscosity of the composition. Fluid viscosity also permits suspension of the proppant in the composition during the fracturing operation. Polysaccharides and cellulosic polymers or their derivatives are typically used to provide viscosity in these fluids. Cross-linking agents, such as borates, titanates or zirconates are usually incorporated into the fluid composition to control viscosity.

Typically, less than one third of available oil is extracted from a well after it has been fractured before production rates decrease to a point at which recovery becomes uneconomical. Enhanced recovery of oil from such subterranean formations frequently involves attempting to displace the remaining crude oil with a driving fluid, e.g., gas, water, brine, steam, polymer solution, foam, or micellar solution. Ideally, such techniques (commonly called flooding techniques) provide a bank of oil of substantial depth being driven into a producing well; however, in practice this is frequently not the case. Oil-bearing strata are usually heterogeneous, some parts of them being more permeable than others. As a consequence, channeling frequently occurs, so that the driving fluid flows preferentially through permeable zones depleted of oil (so-called "thief zones") rather than through those parts of the strata which contain sufficient oil to make oil-recovery operations profitable.

Difficulties in oil recovery due to thief zones may be corrected by injecting an aqueous solution of an organic polymer and a cross-linking agent into a subterranean formation under conditions where the polymer will be cross-linked to produce a gel, thus reducing permeability of the subterranean formation to driving fluid (gas, water, etc.). Polysaccharide- or partially hydrolyzed polyacrylamide-based fluids cross-linked with certain aluminum, titanium, zirconium, and boron based compounds are used in these enhanced oil recovery applications.

Cross-linked fluids or gels, whether for fracturing a subterranean formation or for reducing permeability of zones in subterranean formation, are now being used in wells under a variety of temperature and pH conditions, where rates of cross-linking with known cross-linking compositions may be unacceptable.

U.S. Pat. No. 4,883,605 discloses a water-soluble zirconium chelate formed from a tetraalkyl zirconate and hydroxyethyl-tris-(2-hydroxypropyl)ethylenediamine, and the use of the chelate as a cross-linking agent in hydraulic fracturing fluids and in gels that are used for selectively plugging permeable zones in subterranean formations or for plugging subterranean leaks. Co-pending U.S. patent application Ser. No. 11/643,513, filed Dec. 21, 2006, discloses a related complex having a 1:1 molar ratio of zirconium and N,N,N',N'-tetrakis-(2-hydroxypropyl)-ethylenediamine.

The products of U.S. Pat. No. 4,883,605 and U.S. patent application Ser. No. 11/6,435,513 may be used as cross-linkers for use in many hotter, deeper oil well applications. However, at high pH conditions (such as pH 10), where polysaccharides are most stable, the products of U.S. Pat. No. 4,883,605 cross-link too slowly (>10 minutes), causing a "sand out" to occur, which is the result of sand depositing at the bottom of the wellbore due to lack of viscosity development before the gel reaches the fracture zone. The products of co-pending U.S. patent application Ser. No. 11/643,513 cross-link in the desirable range, which is 3-8 minutes, as illustrated by testing in a FANN viscometer at 275° F. (135° C.) and 122 rpm at 212 reciprocal second of shear. (The FANN results provide a means to predict performance in oil well operation.) Although the products of co-pending U.S. patent application Ser. No. 11/643,513 can be used in many hotter, deeper wells, they do not generate as high a viscosity as desired to maintain the sand in suspension for the length of time needed in hotter, deeper wells having high pH.

Commercially available zirconate cross-linkers, such as tetra-triethanolamine zirconate cross-link too fast under high pH conditions, causing a significant loss in viscosity due to shear degradation, which can also result in sand out. Nonetheless, it is desirable to use a cross-linking composition at pH 10 or higher, where polysaccharides used in cross-linking compositions are most stable.

There is a need for compositions which cross-link at a rate intermediate between zirconium complexes of hydroxyethyl-tris-(2-hydroxypropyl)-ethylenediamine and triethanolamine zirconates at high pH (about pH 10 and above) conditions.

SUMMARY OF THE INVENTION

The present invention provides an effective cross-linking agent which is a zirconium triethanolamine complex, produced by a process which comprises contacting a zirconium triethanolamine complex having a molar ratio of 1:2 to 1:4 of zirconium to triethanolamine with N,N,N',N'-tetrakis-(2-hydroxypropyl)-ethylene diamine wherein the molar ratio of zirconium to N,N,N',N'-tetrakis-(2-hydroxypropyl)-ethylene diamine is 1:0.1 to 1:1. The temperature for the contacting step can be in the range of 25° C. to 90° C. The reaction is typically performed in the presence of an organic solvent.

The present invention also provides a cross-linking composition which comprises (a) an aqueous liquid, (b) a cross-linkable organic polymer, and (c) a solution comprising a zirconium cross-linking agent which comprises a zirconium complex having a molar ratio of 1:2 to 1:4 of zirconium to triethanolamine and a molar ratio of 0.1:1 to 1:1 of zirconium to N,N,N',N'-tetrakis-(2-hydroxypropyl)-ethylene diamine. Optionally, a solvent may be further added to the cross-linking composition.

The cross-linking composition of this invention is useful in oil field applications, for example, for hydraulically fracturing a subterranean formation using the composition. The composition of this invention is further useful for plugging permeable zones or leaks in a subterranean formation. The components of the cross-linking composition may be mixed prior to introducing them into the formation or the components can be introduced and permitted to react in the formation after a controllable period of time.

Surprisingly, in view of known cross-linking compositions comprising zirconium-triethanolamine complexes, the cross-linking composition of this invention has a desirable cross-linking rate of 3-8 minutes and generates good viscosity, preferably in the range of 500 to 1000 centipoise (cp) after 90 minutes at pH 10 by simulation in a FANN viscometer at 275° F. (135° C.) and 122 rpm at 212 reciprocal second of shear. If viscosity is too high, gel syneresis occurs wherein there is over-cross-linking of the polymer and water separates from the gel causing globules of the gel to form, which can no longer suspend the sand or other proppant.

This invention provides a method for hydraulically fracturing a subterranean formation which comprises using a cross-linking composition as described herein. This method comprises introducing into a subterranean formation at a flow rate and pressure sufficient to create, reopen and/or extend a fracture in the formation, (a) an aqueous liquid, (b) a cross-linkable organic polymer, and (c) a solution comprising a zirconium cross-linking agent which comprises a zirconium complex having a molar ratio of 1:2 to 1:4 of zirconium to triethanolamine and a molar ratio of 1:0.1 to 1:1 of zirconium to N,N,N',N'-tetrakis-(2-hydroxypropyl)-ethylene diamine.

This invention provides a method for plugging a permeable zone or leak in a subterranean formation which comprises introducing into said zone or said leak, (a) an aqueous liquid, (b) a cross-linkable organic polymer, and (c) a solution comprising a zirconium cross-linking agent which comprises a zirconium complex having a molar ratio of 1:2 to 1:4 of zirconium to triethanolamine and a molar ratio of 1:0.1 to 1:1 of zirconium to N,N, N',N'-tetrakis-(2-hydroxypropyl)-ethylene diamine.

The present invention provides methods for effective viscosity generation in oil field applications such as fluid fracturing and plugging permeable zones. Surprisingly, the cross-linking composition of this invention cross-links to achieve maximum viscosity in a desirable 3 to 8 minute range at well temperatures, such as 121-177° C. (250-350° F.), especially at temperatures of 135-163° C. (275-325° F.), whereas in general, triethanolamine zirconium complexes have rates of cross-linking that are too fast, or when combined with large volumes of water or at high mole ratios of triethanolamine:zirconium, the rates of cross-linking of triethanolamine zirconium complexes are too slow.

DETAILED DESCRIPTION OF THE INVENTION

Trademarks and trade names used herein are shown in upper case.

This invention provides an effective cross-linking agent or cross-linker for use in cross-linking compositions for oil field applications. The zirconium cross-linking agent can be prepared by modifying a known zirconium cross-linking agent for oil field applications, i.e., a zirconium triethanolamine complex solution.

Zirconium triethanolamine complex solution may be purchased as TYZOR TEAZ organic zirconate, available from E. I. du Pont de Nemours and Company, Wilmington, Del. Alternatively, zirconium triethanolamine complex solution may be prepared by a process which comprises contacting a solution of a tetraalkyl zirconate in a $C_1$-$C_6$ alcohol with two to four molar equivalents of triethanolamine (TEA) to produce an initial reaction product. A number of tetraalkyl zirconates (also known as zirconium tetraalkoxides) can be used to prepare the triethanolamine zirconate solution used in the present invention, e.g., tetra-i-propyl zirconate, tetra-n-propyl zirconate, and tetra-n-butyl zirconate. The preferred tetraalkyl zirconate is tetra-n-propyl zirconate, available as TYZOR NPZ organic zirconate, a solution in n-propanol, with a zirconium content as $ZrO_2$ of about 28% by weight, available from E. I. du Pont de Nemours and Company, Wilmington, Del.

Zirconium triethanolamine complex solution is modified by adding from 0.1 to 1.0 molar equivalents of N,N,N',N'-tetrakis-(2-hydroxypropyl)ethylenediamine per mole of zirconium to provide a solution comprising a zirconium cross-linking agent which comprises a zirconium complex having a molar ratio of 1:2 to 1:4 of zirconium to triethanolamine and a molar ratio of 1:0.1 to 1:1 of zirconium to N,N,N',N'-tetrakis-(2-hydroxypropyl)-ethylene diamine. The ethylenediamine derivative is available commercially, for example, from BASF Corporation, Mount Olive, N.J., under the name QUADROL polyol. Contacting triethanolamine zirconate complex with the hydroxyl alkylated diamine derivative can be carried out at a variety of temperatures, e.g., between 25° C. and 90° C., preferably between 50° C. and 80° C.

The present invention provides a cross-linking composition which comprises (a) an aqueous liquid, (b) a cross-linkable organic polymer, and (c) a solution comprising a zirconium cross-linking agent which comprises a zirconium complex having a molar ratio of 1:2 to 1:4 of zirconium to triethanolamine and a molar ratio of 1:0.1 to 1:1 of zirconium to N,N,N',N'-tetrakis-(2-hydroxypropyl)-ethylene diamine. Optionally, a solvent may be further added to the cross-linking composition.

The aqueous liquid (a) is typically selected from the group consisting of water, aqueous salt solutions, and mixed water/organic solvent. Organic solvents that may be used include alcohols, glycols, polyols, and hydrocarbons such as diesel. Preferably, the aqueous liquid is water, aqueous methanol, aqueous ethanol, or an aqueous solution of a clay stabilizer. Clay stabilizers include, for example, hydrochloric acid and chloride salts, such as, tetramethylammonium chloride (TMAC) or potassium chloride. Preferred stabilizers are TMAC and potassium chloride.

The composition further comprises a cross-linkable organic polymer (b). Suitable cross-linkable organic polymers are selected from the group consisting of solvatable polysaccharides, polyacrylamides and polymethacrylamides. Preferably the organic polymer is a solvatable polysaccharide and is selected from the group consisting of gums, gum derivatives and cellulose derivatives. Gums include guar gum and locust bean gum, as well as other galactomannan and glucomannan gums, such as those derived from sennas, Brazilwood, tera, honey locust, karaya gum and the like. Gum derivatives include hydroxyethylguar (HEG), hydroxypropylguar (HPG), carboxyethylhydroxyethylguar (CEHEG), carboxymethylhydroxypropylguar (CMHPG), carboxymethyl guar (CMG), and the like. Cellulose derivatives include those containing carboxyl groups, such as carboxymethylcellulose (CMC), carboxymethylhydroxyethylcellulose (CMHEC), and the like. The solvatable polysaccharides can be used individually or in combination; usually, however, a single material is used. Guar derivatives and cellulose derivatives are preferred, such as, HPG, CMC and CMHPG. HPG is generally more preferred based upon its commercial availability and desirable properties. However, CMC and CMHPG may be more preferred in cross-linking compositions when the pH of the composition is less than 6.0 or higher than 9.0, or when the permeability of the formation is such that one wishes to keep the residual solids at a low level to prevent damage to the formation.

The solution comprising zirconium cross-linking agent (c) is the triethanolamine zirconate solution modified with N,N,N',N'-tetrakis-(2-hydroxypropyl)ethylenediamine as described previously. Optionally this solution may contain an added organic solvent. Organic solvents that may be used include, for example, alcohols, glycols, and polyols.

The cross-linkable polymer is normally mixed with the aqueous liquid such as water or mixed water/organic solvent or with an aqueous solution to form a base gel. As an example, the aqueous liquid is selected from the group consisting of water, aqueous alcohol (e.g., where the alcohol is methanol or ethanol), and an aqueous solution comprising a clay stabilizer. Clay stabilizers include, for example, hydrochloric acid and chloride salts, such as, tetramethylammonium chloride (TMAC) or potassium chloride. Aqueous solutions comprising clay stabilizers may comprise, for example, 0.05 to 0.5 weight % of the stabilizer, based on the total weight of the cross-linking composition.

The composition may comprise optional components, including those which are common additives for oil field applications. Thus, the composition may further comprise one or more of proppants, friction reducers, bactericides, hydrocarbons, chemical breakers, stabilizers, surfactants, formation control agents, and the like. Proppants include sand, bauxite, glass beads, nylon pellets, aluminum pellets and similar materials. Friction reducers include polyacrylamides. Hydrocarbons include diesel oil. Chemical breakers break the cross-linked polymer (gel) in a controlled manner and include enzymes, alkali metal persulfate, and ammonium persulfate. Stabilizers include clay stabilizers such as hydrochloric acid and chloride salts, for example, tetramethylammonium chloride (TMAC) or potassium chloride. Stabilizers may also include methanol, alkali metal thiosulfate, and ammonium thiosulfate.

These optional components are added in an effective amount sufficient to achieve the desired cross-linking performance based on the individual components, desired cross-linking time, temperature and other conditions present in the formation being fractured or permeable zone being plugged.

The base gel may further comprise an effective amount of a pH buffer to control pH. In the present invention, the buffer is preferably a sodium carbonate or sodium hydroxide-based buffer, which provides a pH of 9-12, preferably about pH 10. Other suitable pH buffers can be used, as are known to those skilled in the art. Less preferred are acidic or neutral pH buffers. For example, in a composition for use at pH of about 4-5, an acetic acid-based buffer can be used. In a composition for use at a pH of 5-7, a fumaric acid-based buffer or a sodium diacetate-based buffer can be used. In a composition for use at a pH of 7-8.5, a sodium bicarbonate-based buffer can be used.

The cross-linking composition is produced by mixing the solution comprising zirconium cross-linking agent with the other components, in any order. For example, in one particular application in an oil field, the solution of zirconium cross-linking agent and optional components are introduced into a formation, while the cross-linkable organic polymer and aqueous liquid are introduced into the formation as a separate stream. Alternatively, all components may be premixed and introduced into a subterranean formation as a single stream. Advantageously, the components may be mixed in different combinations, and more advantageously, the components may be mixed just prior to use to enable easy variation and adjustment of the cross-linking rate.

This invention provides a method for hydraulically fracturing a subterranean formation, which comprises introducing into the formation at a flow rate and pressure sufficient to create, reopen, and/or extend one or more fractures in the formation, an aqueous liquid, a cross-linkable organic polymer, and a solution of a zirconium cross-linking agent comprising a zirconium complex having a molar ratio of 1:2 to 1:4 of zirconium to triethanolamine and a molar ratio of 1:0.1 to 1:1 of zirconium to N,N,N',N'-tetrakis-(2-hydroxypropyl)-ethylene diamine. A solvent and other optional components may also be added.

In one embodiment of the method for hydraulically fracturing a subterranean formation, the solution comprising zirconium cross-linking agent and the cross-linkable polymer are contacted prior to their introduction into the formation, such that the cross-linking agent and polymer react to form a cross-linked gel. The gel is then introduced into the formation at a flow rate and pressure sufficient to create, reopen, and/or extend a fracture in the formation.

In this method, a base gel is prepared by mixing a cross-linkable organic polymer with an aqueous liquid. The cross-linked gel composition is prepared by mixing the base gel with the solution comprising zirconium cross-linking agent. Optionally the zirconium solution may contain an added solvent. The base gel may further comprise a pH buffer.

Alternatively, the subterranean formation may be penetrated by a wellbore, such that contacting the solution of zirconium cross-linking agent with the base gel occurs in the wellbore and the cross-linked gel is introduced into the formation from the wellbore. This method of hydraulically fracturing a subterranean formation penetrated by a wellbore comprises (a) preparing a base gel by mixing a cross-linkable organic polymer with an aqueous liquid; (b) introducing the base gel into the wellbore; (c) simultaneously with or sequentially after, introducing the base gel into the wellbore, introducing into the wellbore, a solution comprising a zirconium cross-linking agent which comprises a zirconium complex having a molar ratio of 1:2 to 1:4 of zirconium to triethanolamine and a molar ratio of 1:0.1 to 1:1 of zirconium to N,N,N',N'-tetrakis-(2-hydroxypropyl)-ethylene diamine; (d) permitting the base gel and the solution of zirconium cross-linking agent to react to form a cross-linked aqueous gel; and (e) introducing the cross-linked gel into the formation from the wellbore at a flow rate and pressure sufficient to create, reopen, and/or extend a fracture in the formation. A pH buffer may be independently admixed with the base gel prior to introducing the base gel and the zirconium solution into the wellbore.

Upon creation of a fracture or fractures, the method may further comprise introducing a cross-linking composition comprising the solution of zirconium cross-linking agent, a cross-linkable organic polymer and proppant into the fracture or fractures. This second introduction of a solution of zirconium cross-linking agent is preferably performed in the event the cross-linking composition used to create the fracture or fractures did not comprise proppant.

Another use for the solution of zirconium cross-linking agent of the present invention relates to a method for selectively plugging permeable zones and leaks in subterranean formations which comprises introducing into the permeable zone or the site of the subterranean leak, an aqueous liquid, a cross-linkable organic polymer, and a solution comprising a zirconium cross-linking agent which comprises a zirconium complex having a molar ratio of 1:2 to 1:4 of zirconium to triethanolamine and a molar ratio of 1:0.1 to 1:1 of zirconium to N,N,N',N'-tetrakis-(2-hydroxypropyl)-ethylene diamine, into the permeable zone or the site of the subterranean leak.

In a first embodiment of the method for plugging a permeable zone or a leak in a subterranean formation, the aqueous liquid, cross-linkable organic polymer and the solution comprising zirconium cross-linking agent are contacted prior to their introduction into the subterranean formation, such that the polymer and zirconium complex react to form a cross-linked aqueous gel, which gel is then introduced into the formation.

In an alternative embodiment of the method for plugging a permeable zone or a leak in a subterranean formation, the solution comprising zirconium cross-linking agent and the cross-linkable organic polymer are introduced separately, either simultaneously or sequentially, into the permeable zone or the site of the subterranean leak such that cross-linking occurs within the subterranean formation. This method comprises (a) preparing a base gel by mixing a cross-linkable organic polymer with an aqueous liquid; (b) introducing the base gel into the into the permeable zone or the site of the subterranean leak; (c) simultaneously with or sequentially after, introducing the base gel into the into the permeable zone or the site of the subterranean leak, introducing the solution comprising zirconium cross-linking agent into the into the permeable zone or the site of the subterranean leak; (d) permitting the base gel and the cross-linking agent to react to form a cross-linked aqueous gel to plug the zone and/or leak. The base gel may further comprise a pH buffer.

The relative amounts of cross-linkable organic polymer and the zirconium complex may vary. One uses small but effective amounts which for both will vary with the conditions, e.g., the type of subterranean formation, the depth at which the method (e.g., fluid fracturing, permeable zone plugging or leak plugging) is to be performed, temperature, pH, etc. Generally one uses as small an amount of each component as will provide the viscosity level necessary to effect the desired result, i.e., fracturing of the subterranean formation, or plugging permeable zones or leaks to the extent necessary to promote adequate recovery of oil or gas from the formation.

For example, satisfactory gels can generally be made for fluid fracturing by using the cross-linkable organic polymer in amounts up to about 1.2 weight % typically in the range of 0.1 to 1.2 weight %, based on the total weight of the gel. The cross-linking composition is used in amounts that provide 0.01 to 0.50 weight % of the zirconium complex, based on the total weight of the gel. Preferably, from about 0.25 to about 0.75 weight % of the cross-linkable organic polymer is used and from about 0.05 to about 0.25 weight % of the zirconium complex is used.

In a method for plugging permeable zones or leaks, generally about 0.25 to 1.2 weight % of a cross-linkable organic polymer is used, preferably 0.40 to 0.75 weight %, based on the total weight of the gel. Generally about 0.01 to 0.50 weight % of the zirconium complex is used, preferably 0.05 to 0.25 weight %, based on the total weight of the gel.

The amount of zirconium complex used to cross-link the organic polymer is that which provides a zirconium ion concentration in a range from about 0.0005 weight % to about 0.1 weight %, based on the total weight. The preferred concentration of zirconium ion is in the range of from about 0.001-0.05 weight %, based on the total weight.

The solution of zirconium cross-linking agent and the cross-linking composition of this invention can be used at a pH of from about 3 to 11. For low temperature applications (150-250° F., 66-121° C.), carbon dioxide-based energized fluids may be used. In this case, a pH for the cross-linking composition of about 3 to about 6 is preferred. For moderate or high temperature applications (250-400° F., 121-204° C.), a pH of about 9 to about 11 is preferred, more preferably pH 10. Advantageously, the solution of zirconium cross-linking agent and the cross-linking composition of this invention is used at a temperature of 275-325° F. (135-163° C.).

EXAMPLES

The preparation of the compositions in the Examples and in the Controls were each carried out in closed vessels containing an agitator, thermometer, condenser, nitrogen inlet and dropping funnel. Unless specified otherwise, percentages are given by weight. Temperatures are given in degrees Celsius. The cross-linking properties of the compositions of the Examples are provided as a function of the viscosity of carboxymethylhydroxypropylguar (CMHPG) cross-linked with the zirconate.

Control 1

Triethanolamine (135.2 g) was added to 100 g of tetra-n-propyl zirconate solution (TYZOR NPZ organic zirconate, available from E. I. du Pont de Nemours and Company, Wilmington, Del.). The reaction mixture was heated to 60° C. and held there for 4 hours. Upon completion of the reaction the resultant solution of tetra(triethanolamine)zirconate was concentrated on a rotary evaporator under reduced pressure to yield 155 g of a viscous yellow oil, which contained 13.2% Zr.

Control 2

Hydroxyethyl-tris-(2-hydroxypropyl)ethylenediamine (146 g) was added to 220.3 g of tetra-n-propyl zirconate. The reaction mixture was heated to 60° C. and held there for 4 hours to give 346 g of a pale yellow liquid containing hydroxyethyl-tris-(2-hydroxypropyl)ethylenediamine zirconate, containing 12.4% Zr.

Comparative Example A

Tetra-2-hydroxypropyl ethylenediamine, QUADROL polyol, (66.3 g) was added to 100 g of tetra-n-propyl zirconate (TYZOR NPZ organic zirconate) in a 1:1 mole ratio of the diamine to zirconium. The resultant mixture was heated to 60° C. and held there for 2 hours. During the heating period, a white solid separated from the reaction mass. Upon dilution with 4.1 g of water, the solids dissolved. The resultant solution of zirconium complex of tetra-2-hydroxypropyl ethylenediamine was heated an additional 4 hours at 80° C. to give a 170 g of a pale yellow liquid containing 12.1% Zr.

Example 1

A 500 ml flask, equipped with a thermocouple, dropping funnel, N2 bleed and condenser was charged with 100 g of TYZOR NPZ organic zirconate. Agitation was started and 135.3 g of triethanolamine was added. The mixture was heated for 2 hours at 60° C. and then 33.2 g of QUADROL polyol was added. The solution was heated at 60° C. for another 2 hours to give 268 g of a stable solution containing 7.7% Zr.

Example 2

A 500 ml flask, equipped with a thermocouple, dropping funnel, N2 bleed and condenser was charged with 100 g of TYZOR NPZ organic zirconate. Agitation was started and 135.3 g of triethanolamine was added. The mixture was heated for 2 hours at 60° C. and then 66.3 g of QUADROL polyol was added. The solution was heated at 60° C. for another 2 hours to give 300 g of a stable solution containing 6.9% Zr.

Example 3

A 500 ml flask, equipped with a thermocouple, dropping funnel, N2 bleed and condenser was charged with 100 g of TYZOR NPZ organic zirconate. Agitation was started and 67.7 g of triethanolamine and 33.2 g of QUADROL polyol was added. The solution was heated to 60° C. and held 2 hours. On cooling 34.7 g of n-propanol was added to give 234 g of a clear, orange solution containing 8.8% Zr.

Example 4

A 500 ml flask, equipped with a thermocouple, dropping funnel, N2 bleed and condenser was charged with 100 g of TYZOR NPZ organic zirconate. Agitation was started and 67.7 g of triethanolamine and 66.3 g of QUADROL polyol was added. The solution was heated to 60° C. and held 2 hours to give 234 g of a clear, orange solution containing 8.8% Zr.

Preparation of Base Gel

A Waring blender jar was filled with 1 liter of distilled water. To this was added 2 g of a 50% aqueous solution of tetramethylammonium chloride clay stabilizer. Agitation was started and 3.6 g of carboxymethylhydroxypropylguar (CM-HPG) was sprinkled into the vortex of the agitating solution. The pH of the resultant slurry was adjusted to 6 with sodium diacetate and agitation continued for 30 minutes. The pH was then adjusted to 10.3 with 10% sodium hydroxide solution. Agitation was stopped and the gel was allowed to stand for 30 minutes or more before use.

Viscosity Measurement of Zirconate Cross-Linked Base Gel

To 250 ml of a vigorously agitated sample of base gel in a Waring blender jar, was added 0.00032 moles of zirconium (0.2-1.0 ml dependent on percent zirconium of cross-linker solution—hereinafter referred to as the Standard Loading Density). Agitation was continued for about 15-180 seconds. A 25 ml sample of the cross-linker containing gel was placed in the cup of the FANN 50 Viscometer with an R-1, B-3 configuration and viscosity was measured at 275° F. (135° C.) and 122 rpm at 212 reciprocal seconds of shear.

Table 1 shows the performance of a 30 lb/1000 gallon (3600 g/1000 liters) CMHPG gel cross-linked with both known zirconates (Controls) and those of the invention. In this Table, "Zr, %" refers to the weight percent of zirconium in the zirconium solutions produced in Controls and Examples. "Zr, soln., ml" refers to the volume of zirconium complex solution added to the base gel. "Zr, moles" refers to the number of moles of Zr added to the base gel. "Alkanol amine" refers to the alkanol amine added; TEA is triethanolamine; "L-699" is hydroxyethyl-tris-(2-hydroxyisopropyl) ethylenediamine. Moles of alkanol amine added are provided in parentheses. "Hydroxyl alkylated amine" refers to the hydroxylated amine added, wherein in these examples, the hydroxylated amine is QUADROL polyol. Moles of added the hydroxylated amine added are provided in parentheses. "Water (moles)" refers to the amount of water added, with moles in parentheses. "Fann Time max" means the time, in minutes, for the cross-linked gel to reach maximum viscosity, after zirconium solution is added to base gel. "Viscosity@time max" means the maximum viscosity, in centipoise (cp) that is reached at Fann Time max. "Viscosity@90 min." means the viscosity, in cp, of the gel 90 minutes after zirconium solution is added to base gel.

As can be seen from the Table, the zirconium-triethanolamine cross-linking composition in Control 1 generates excellent viscosity; however its rate of cross-linking, as measured by time to reach maximum viscosity, is much too fast at 1.5 minutes. In the field, at this rate of cross-linking, it would be expected that shear degradation and loss of viscosity of the cross-linked gel would occur prior to reaching the zone to be fractured or plugged in the formation.

The rate of cross-linking for Control 2, the hydroxyethyl-tris-(2-hydroxypropyl)ethylenediamine zirconium complex, is too slow. In the field, viscosity generation is so slow that at this slow rate of cross-linking, sand would be expected to drop out of the cross-linking fluid before the fluid reached the zone to be fractured.

As can be seen from the Table, the rate of cross-linking for the triethanolamine zirconium complex of co-pending U.S. patent application Ser. No. 11/643,513, filed Dec. 21, 2006 (Comparative Example A) cross-links in the desirable 3-8 minute range; however, viscosity development and retention is less than desired for the highest temperature wells. In the field, this would result in sand being deposited prematurely, causing less than desired oil recovery. Alternatively, a higher loading of polymer may be required (resulting in higher costs) to provide sufficient viscosity.

The cross-linking rates containing the solutions of this invention in Examples 1-4 are within the desirable range of 3-8 minutes and viscosity development and retention are excellent. At these cross-linking rates, the cross-linking compositions can be used in the field for fracturing or plugging, even for hotter, deeper formations. In addition, greater viscosity retention at 90 minutes, indicates a stronger cross-linker and ability to use less polymer (lowering costs) in practice.

What is claimed is:

1. A cross-linking composition comprising (a) an aqueous liquid; (b) a cross-linkable organic polymer; and (c) a solution comprising a zirconium cross-linking agent which comprises a zirconium complex having a 1:2 to 1:4 molar ratio of zirconium to triethanolamine and a 1:0.1 to 1:1 molar ratio of zirconium to N,N,N',N'-tetrakis-(2-hydroxypropyl)-ethylene diamine and wherein the cross-linking composition has a cross-linking rate of 3-8 minutes generating viscosity in the range of 500 to 1000 centipoise (cp) after 90 minutes at pH 10 by simulation in a FANN viscometer at 275° F. (135° C.) and 122 rpm at 212 reciprocal second of shear.

2. The cross-linking composition of claim 1 wherein the cross-linkable organic polymer is selected from the group consisting of solvatable polysaccharides, polyacrylamides and polymethacrylamides.

3. The cross-linking composition of claim 2 wherein the cross-linkable organic polymer is a solvatable polysaccharide.

TABLE 1

Performance Results

| Example | Zr, % | Zr soln., ml | Zr, moles | Alkanol amine (moles) | Hydroxyl alkylated diamine (moles) | Water (moles) | Fann Time max., min. | Viscosity @ time max., Cp | Viscosity @ 90 min., Cp |
|---|---|---|---|---|---|---|---|---|---|
| Control 1 | 13.2 | 0.18 | 1 | TEA (4) | | | 1.5 | 1125 | 660 |
| Control 2 | 12.4 | 0.27 | 1 | L-699 (1) | | | 12 | 300 | 225 |
| Comparative A | 12.1 | 0.24 | 1 | | QUADROL (1) | 1 | 7 | 650 | 445 |
| 1 | 7.7 | 0.39 | 1 | TEA (4) | QUADROL (0.5) | | 4 | 1375 | 925 |
| 2 | 6.9 | 0.43 | 1 | TEA (4) | QUADROL (1) | | 3 | 800 | 610 |
| 3 | 8.8 | 0.34 | 1 | TEA (2) | QUADROL (0.5) | | 4.5 | 1245 | 810 |
| 4 | 8.8 | 0.34 | 1 | TEA (2) | QUADROL (1) | | 7.5 | 825 | 580 |

4. The cross-linking composition of claim 3 wherein the cross-linkable organic polymer is selected from the group consisting of gums, gum derivatives and cellulose derivatives.

5. The cross-linking composition of claim 4 wherein the cross-linkable organic polymer is hydroxypropylguar, carboxymethylhydroxypropylguar, or carboxymethylcellulose.

6. The cross-linking composition of claim 1 further comprising a solvent.

7. The cross-linking composition of claim 1 wherein the cross-linkable polymer is mixed with the aqueous liquid to form a base gel and wherein the base gel comprises a pH buffer.

8. The cross-linking composition of claim 7 wherein the pH buffer is a sodium carbonate or sodium hydroxide-based buffer to control pH at pH 9 to 12.

9. The cross-linking composition of claim 3 wherein the aqueous liquid is selected from the group consisting of water, aqueous salt solutions and mixed water/organic solvent.

10. The cross-linking composition of claim 9 wherein the aqueous liquid is water, aqueous methanol, aqueous ethanol, an aqueous solution of tetramethylammmonium chloride or an aqueous solution of potassium chloride.

11. A method for hydraulically fracturing a subterranean formation comprising introducing into a subterranean formation at a flow rate and pressure sufficient to create, reopen and/or extend a fracture in the formation, (a) an aqueous liquid; (b) a cross-linkable organic polymer; and (c) a solution comprising a zirconium cross-linking agent which comprises a zirconium complex having a 1:2 to 1:4 molar ratio of zirconium to triethanolamine and a 1:0.1 to 1:1 molar ratio of zirconium to N,N,N',N'-tetrakis-(2-hydroxypropyl)-ethylene diamine and wherein the cross-linking composition has a cross-linking rate of 3-8 minutes generating viscosity the range of 500 to 1000 centipoise (cp) after 90 minutes at pH 10 by simulation in a FANN viscometer at 275° F. (135° C.) and 122 rpm at 212 reciprocal second of shear .

12. The method of claim 11 wherein the aqueous liquid, cross-linkable organic polymer; and solution comprising zirconium cross-linking agent are contacted prior to their introduction into the subterranean formation.

13. The method of claim 11 wherein the subterranean formation is penetrated by a wellbore and wherein the method comprises (a) preparing a base gel by mixing the cross-linkable organic polymer with the aqueous liquid; (b) introducing the base gel into the wellbore; (c) simultaneously with or sequentially after, introducing the base gel into the wellbore, introducing the solution comprising zirconium cross-linking agent into the wellbore; (d) permitting the base gel and the solution comprising zirconium cross-linking agent to react in the wellbore to form a cross-linked aqueous gel; and (e) introducing the cross-linked gel into the formation from the wellbore at a flow rate and pressure sufficient to create, reopen, and/or extend a fracture in the formation.

14. The method of claim 11 or 13 further comprising introducing proppant into the subterranean formation.

15. The method of claim 11 or 13 wherein the pH is in the range of 9-12.

16. The method of claim 15 wherein the temperature of the formation is in the range of 250-400° F. (121-204° C.).

17. The method of claim 16 wherein the temperature is in the range of 275-325° F. (135-163° C.).

18. The method of claim 11 wherein the amount of cross-linkable organic polymer present in the cross-linked gel is in the range of 0.1 to 1.2 weight %; the amount of zirconium cross-linking agent is in the range of 0.01 to 0.50 weight %.

19. The method of claim 18 wherein the amount of cross-linkable organic polymer present in the cross-linked gel is in the range of 0.25 to 0.75 weight %, and the amount of zirconium complex is in the range of 0.05 to 0.25 weight %.

20. A method for plugging a permeable zone or leak in a subterranean formation comprising introducing into said zone or said leak, (a) an aqueous liquid; (b) a cross-linkable organic polymer; and (c) a solution comprising a zirconium cross-linking agent which comprises a zirconium complex having a 1:2 to 1:4 molar ratio of zirconium to triethanolamine and a 1:0.1 to 1:1 molar ratio of zirconium to N,N,N',N'-tetrakis-(2-hydroxypropyl)-ethylene diamine and wherein the cross-linking composition has a cross-linking rate of 3-8 minutes generating viscosity in the range of 500 to 1000 centipoise (cp) after 90 minutes at pH 10 by simulation in a FANN viscometer at 275° F. (135° C.) and 122 rpm 212 reciprocal second of shear.

21. The method of claim 20 wherein the aqueous liquid, cross-linkable organic polymer; and solution comprising zirconium cross-linking agent are contacted prior to their introduction into the subterranean formation.

22. The method of claim 20 wherein the solution comprising zirconium cross-linking agent and the cross-linkable organic polymer are introduced separately into the permeable zone or the site of the subterranean leak such that cross-linking occurs within the subterranean formation.

23. The method of claim 20 comprising (a) preparing a base gel by mixing a cross-linkable organic polymer with an aqueous liquid; (b) introducing the base gel into the into the permeable zone or the site of the subterranean leak; (c) simultaneously with or sequentially after, introducing the base gel into the into the permeable zone or the site of the subterranean leak, introducing the solution comprising zirconium cross-linking agent into the into the permeable zone or the site of the subterranean leak; (d) permitting the base gel and the cross-linking agent to react to form a cross-linked aqueous gel to plug the zone and/or leak.

24. The method of claim 20 or 22 wherein the pH is in the range of 9-12.

25. The method of claim 24 wherein the temperature of the formation is in the range of 250-400° F. (121-204° C.).

26. The method of claim 25 wherein the temperature is in the range of 275-325° F. (135-163° C.).

27. The method of claim 20 wherein the amount of cross-linkable organic polymer present in the cross-linked gel is in the range of 0.25 to 1.2 weight %; the amount of zirconium cross-linking agent is in the range of 0.01 to 0.50 weight %.

28. The method of claim 20 wherein the amount of cross-linkable organic polymer present in the cross-linked gel is in the range of 0.40 to 0.75 weight %, and the amount of zirconium cross-linking agent is in the range of 0.05 to 0.25 weight %.

* * * * *

UNITED STATES PATENT AND TRADEMARK OFFICE
CERTIFICATE OF CORRECTION

PATENT NO. : 8,236,739 B2  Page 1 of 1
APPLICATION NO. : 11/731049
DATED : August 7, 2012
INVENTOR(S) : Donald Edward Putzig It is certified that error appears in the above-identified patent and that said Letters Patent is hereby corrected as shown below:

On the Title Page, Item [73] assignee, replace "Dork Ketal Speciality Catalysts, LLC" with
-- Dorf Ketal Speciality Catalysts, LLC --

Signed and Sealed this
Twenty-ninth Day of January, 2013

David J. Kappos
*Director of the United States Patent and Trademark Office*